(12) United States Patent
Barrow-Williams

(10) Patent No.: US 8,313,464 B2
(45) Date of Patent: Nov. 20, 2012

(54) INJECTION DEVICE

(75) Inventor: Tim Barrow-Williams, Melbourn (GB)

(73) Assignee: Cilag GmbH International (CH)

( * ) Notice: Subject to any disclaimer, the term of this patent is extended or adjusted under 35 U.S.C. 154(b) by 521 days.

(21) Appl. No.: 11/579,561

(22) PCT Filed: May 27, 2005

(86) PCT No.: PCT/GB2005/002137
§ 371 (c)(1),
(2), (4) Date: Aug. 27, 2008

(87) PCT Pub. No.: WO2005/115513
PCT Pub. Date: Dec. 8, 2005

(65) Prior Publication Data
US 2009/0012470 A1 Jan. 8, 2009

(30) Foreign Application Priority Data
May 28, 2004 (GB) .................................. 0412061.4

(51) Int. Cl.
*A61M 5/20* (2006.01)
*A61M 5/00* (2006.01)
(52) U.S. Cl. ........................ 604/136; 604/156; 604/110
(58) Field of Classification Search .......... 604/156–157, 604/131–139, 110, 198
See application file for complete search history.

(56) References Cited

U.S. PATENT DOCUMENTS

| | | | |
|---|---|---|---|
| 1,845,036 A | 2/1932 | Busher | |
| 2,019,382 A | 10/1935 | Aronson | |
| 2,531,267 A | 11/1950 | Harisch | |
| 2,764,977 A | 10/1956 | Ferguson | |
| 2,828,742 A | 4/1958 | Ashkenaz | |
| 3,329,146 A | 7/1967 | Waldman | |
| 3,543,603 A | 12/1970 | Gley | |
| 3,656,472 A | 4/1972 | Moura | |
| 3,702,608 A | 11/1972 | Tibbs | |

(Continued)

FOREIGN PATENT DOCUMENTS

CH 518102 A 1/1972
(Continued)

OTHER PUBLICATIONS

International Search Report dated Sep. 5, 2005; International Application No. PCT/GB2005/002117.

(Continued)

*Primary Examiner* — Nicholas Lucchesi
*Assistant Examiner* — Weng Lee

(57) ABSTRACT

An injection device (210) is described. A housing (212) receives a syringe and includes a return spring (226) for biasing the syringe from an extended position in which its needle (218) extends from the housing (212) to a retracted position in which the it does not. A drive spring (230) acts on a first drive element (232) and a second drive element (234) acts upon the syringe to advance it from its retracted position to its extended position and discharge its contents through the needle. The first drive element (232) is capable of movement relative to the second (234) once a nominal decoupling position has been reached. A release mechanism is activated when the first drive element (234) is further advanced to a nominal release position, to release the syringe (214) from the action of the drive spring (230), whereupon the return spring (226) restores the syringe (214) to its retracted position. A locking mechanism (337, 375) confines the returned syringe in its retracted position.

10 Claims, 3 Drawing Sheets

U.S. PATENT DOCUMENTS

| | | |
|---|---|---|
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,231,368 A | 11/1980 | Becker |
| 4,299,238 A | 11/1981 | Baidwan et al. |
| 4,378,015 A | 3/1983 | Wardlaw |
| 4,394,863 A | 7/1983 | Bartner |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran et al. |
| 4,636,201 A | 1/1987 | Ambrose et al. |
| 4,744,786 A | 5/1988 | Hooven et al. |
| 4,787,891 A | 11/1988 | Levin et al. |
| 4,874,383 A | 10/1989 | McNaughton |
| 4,929,232 A | 5/1990 | Sweeney et al. |
| 4,988,339 A | 1/1991 | Vadher |
| 5,009,646 A | 4/1991 | Sudo et al. |
| 5,026,349 A | 6/1991 | Schmitz et al. |
| 5,092,842 A | 3/1992 | Bechtold et al. |
| 5,098,400 A | 3/1992 | Crouse et al. |
| 5,114,406 A | 5/1992 | Gabriel et al. |
| 5,122,119 A * | 6/1992 | Lucas ............................ 604/138 |
| 5,137,516 A | 8/1992 | Rand et al. |
| 5,141,496 A | 8/1992 | Dalto et al. |
| 5,156,599 A | 10/1992 | Ranford et al. |
| 5,176,643 A | 1/1993 | Kramer et al. |
| 5,190,526 A | 3/1993 | Murray et al. |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,330,430 A | 7/1994 | Sullivan |
| 5,358,489 A | 10/1994 | Wyrick |
| 5,372,586 A | 12/1994 | Haber et al. |
| 5,391,151 A * | 2/1995 | Wilmot .......................... 604/139 |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,514,097 A * | 5/1996 | Knauer .......................... 604/136 |
| 5,520,653 A | 5/1996 | Reilly et al. |
| 5,540,660 A | 7/1996 | Jenson et al. |
| 5,540,709 A | 7/1996 | Ramel et al. |
| 5,567,160 A | 10/1996 | Massino |
| 5,569,192 A * | 10/1996 | van der Wal ..................... 604/84 |
| 5,575,777 A | 11/1996 | Cover et al. |
| 5,599,302 A | 2/1997 | Lilley et al. |
| 5,599,309 A | 2/1997 | Marshall et al. |
| 5,609,577 A | 3/1997 | Haber et al. |
| 5,609,584 A | 3/1997 | Gettig et al. |
| 5,637,094 A | 6/1997 | Stewart, Jr. et al. |
| 5,645,536 A | 7/1997 | Whisson |
| 5,647,845 A | 7/1997 | Haber et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,843,036 A | 12/1998 | Olive et al. |
| 5,868,711 A | 2/1999 | Kramer et al. |
| 5,879,327 A | 3/1999 | DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross et al. |
| 6,159,181 A | 12/2000 | Crossman et al. |
| 6,162,199 A | 12/2000 | Geringer |
| 6,171,276 B1 | 1/2001 | Lippe et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,221,044 B1 | 4/2001 | Greco |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,293,925 B1 | 9/2001 | Safabash et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 * | 10/2002 | Frezza .......................... 604/192 |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Alchas et al. |
| 6,569,124 B1 | 5/2003 | Perouse |
| 6,572,581 B1 | 6/2003 | Landau |
| 6,575,939 B1 | 6/2003 | Brunel |
| 6,585,702 B1 | 7/2003 | Brunel |
| 6,589,210 B1 | 7/2003 | Rolfe |
| 6,595,962 B1 | 7/2003 | Perthu |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landau |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard |
| 6,746,429 B2 | 6/2004 | Sadowski et al. |

| | | |
|---|---|---|
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujita et al. |
| 6,796,967 B2 | 9/2004 | Jensen |
| 6,811,548 B2 | 11/2004 | Jeffrey |
| 6,846,303 B2 | 1/2005 | Eakins et al. |
| 6,890,319 B1 | 5/2005 | Crocker |
| 6,899,698 B2 | 5/2005 | Sams |
| 6,932,793 B1 | 8/2005 | Marshall et al. |
| 6,939,319 B1 | 9/2005 | Anstead et al. |
| 6,979,316 B1 | 12/2005 | Rubin et al. |
| 7,066,907 B2 | 6/2006 | Crossman et al. |
| 7,097,634 B2 | 8/2006 | Gilbert |
| 7,118,553 B2 | 10/2006 | Scherer |
| 7,156,823 B2 | 1/2007 | Landau et al. |
| 7,744,561 B2 | 6/2010 | Stamp |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0049496 A1 | 12/2001 | Kirchhofer et al. |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0015134 A1 | 1/2004 | Lavi et al. |
| 2004/0019326 A1 | 1/2004 | Gilbert et al. |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0020979 A1 | 1/2005 | Westbye et al. |
| 2005/0027255 A1 | 2/2005 | Lavi et al. |
| 2005/0033234 A1 | 2/2005 | Sadowski et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0101919 A1 | 5/2005 | Brunnberg |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0203466 A1 | 9/2005 | Hommann et al. |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184137 A1 | 8/2006 | Reynolds |
| 2006/0224124 A1 | 10/2006 | Scherer |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0078382 A1 | 4/2007 | Hommann et al. |
| 2007/0142787 A1 | 6/2007 | Scherer |
| 2008/0312606 A1 | 12/2008 | Harrison et al. |
| 2009/0054849 A1 | 2/2009 | Burnell et al. |
| 2009/0088688 A1 | 4/2009 | Donald et al. |
| 2010/0016793 A1 | 1/2010 | Jennings et al. |

FOREIGN PATENT DOCUMENTS

| | | |
|---|---|---|
| CN | 2059579 U | 7/1990 |
| CN | 1190599 A | 8/1998 |
| CN | 1541121 A | 10/2004 |
| CN | 1550240 A | 12/2004 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0516473 | 12/1992 |
| EP | 0331452 A2 | 8/1993 |
| EP | 0585626 A1 | 3/1994 |
| EP | 0389938 B1 | 5/1994 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |

| | | | | | | |
|---|---|---|---|---|---|---|
| EP | 1932558 A1 | 6/2008 | | WO | WO 94/04207 A1 | 3/1994 |
| EP | 2023980 A1 | 2/2009 | | WO | WO 94/07554 A1 | 4/1994 |
| EP | 2129414 A1 | 12/2009 | | WO | WO 94/11041 | 5/1994 |
| EP | 1755706 B1 | 3/2010 | | WO | WO 94/13342 A1 | 6/1994 |
| EP | 1928523 B1 | 7/2010 | | WO | WO 94/21316 A1 | 9/1994 |
| EP | 1518575 B1 | 11/2010 | | WO | WO 94/22511 A1 | 10/1994 |
| FR | 1014881 A | 8/1952 | | WO | WO 95/04562 A1 | 2/1995 |
| FR | 1169935 A | 1/1959 | | WO | WO 95/29720 A1 | 11/1995 |
| FR | 1538565 A | 9/1968 | | WO | WO 95/31235 A1 | 11/1995 |
| FR | 2506161 A1 | 11/1982 | | WO | WO 95/35126 A1 | 11/1995 |
| FR | 2629706 A | 10/1989 | | WO | WO 95/35126 A1 | 12/1995 |
| FR | 2654938 A1 | 5/1991 | | WO | 96/30065 A1 | 10/1996 |
| FR | 2665079 A1 | 1/1992 | | WO | WO 97/10865 A1 | 3/1997 |
| FR | 2717086 A1 | 9/1995 | | WO | WO 97/13538 A1 | 4/1997 |
| FR | 2741810 A1 | 6/1997 | | WO | WO 97/48430 A1 | 12/1997 |
| FR | 2861310 A1 | 4/2005 | | WO | WO 98/11927 A1 | 3/1998 |
| GB | 143084 | 5/1920 | | WO | WO 99/03529 A2 | 1/1999 |
| GB | 0412054 | 6/1934 | | WO | WO 99/10030 A2 | 3/1999 |
| GB | 728248 | 4/1955 | | WO | WO 99/22789 A1 | 5/1999 |
| GB | 909898 | 11/1962 | | WO | WO 99/37343 A | 7/1999 |
| GB | 1263355 | 2/1972 | | WO | WO 99/53979 A1 | 10/1999 |
| GB | 1311937 A | 3/1973 | | WO | WO 99/59658 A1 | 11/1999 |
| GB | 1514725 | 6/1978 | | WO | WO 00/06227 A1 | 2/2000 |
| GB | 2338033 A | 12/1999 | | WO | WO 00/07539 A1 | 2/2000 |
| GB | 2388033 A | 11/2003 | | WO | WO 00/13723 A2 | 3/2000 |
| GB | 2396298 A | 6/2004 | | WO | WO 00/24441 A1 | 5/2000 |
| GB | 2396816 A | 7/2004 | | WO | WO 00/35516 | 6/2000 |
| GB | 2397767 A | 8/2004 | | WO | WO 00/50107 A1 | 8/2000 |
| GB | 2414398 A | 11/2005 | | WO | WO 00/64515 A1 | 11/2000 |
| GB | 2414399 A | 11/2005 | | WO | WO 00/69488 A2 | 11/2000 |
| GB | 2414400 A | 11/2005 | | WO | WO 01/05456 A1 | 1/2001 |
| GB | 2414401 A | 11/2005 | | WO | 01/49347 A1 | 7/2001 |
| GB | 2414402 A | 11/2005 | | WO | WO 01/76666 A1 | 10/2001 |
| GB | 2414403 A | 11/2005 | | WO | WO 01/77384 A2 | 10/2001 |
| GB | 2424835 A | 10/2006 | | WO | WO 01/87384 A1 | 11/2001 |
| GB | 2424836 A | 10/2006 | | WO | WO 02/11799 A1 | 2/2002 |
| GB | 2424838 A | 10/2006 | | WO | WO 02/47746 A1 | 6/2002 |
| GB | 2433035 A | 6/2007 | | WO | WO 02/056947 A1 | 7/2002 |
| GB | 2437922 A | 11/2007 | | WO | WO 03/013632 A2 | 2/2003 |
| GB | 2438591 A | 12/2007 | | WO | WO 03/015853 A1 | 2/2003 |
| GB | 2446778 A | 8/2008 | | WO | WO 03/039633 A2 | 5/2003 |
| JP | 59-115053 A | 7/1984 | | WO | WO 03/041768 A | 5/2003 |
| JP | 2-185261 A | 7/1990 | | WO | WO 03/047663 A2 | 6/2003 |
| JP | 2-502971 T | 9/1990 | | WO | WO 03/051434 A2 | 6/2003 |
| JP | 11-501549 T | 2/1992 | | WO | WO 03/066141 A1 | 8/2003 |
| JP | 5-161712 A | 6/1993 | | WO | WO 03/092771 | 11/2003 |
| JP | 6-209996 A | 8/1994 | | WO | WO 03/097133 | 11/2003 |
| JP | 6-508773 T | 10/1994 | | WO | WO 03/099358 A2 | 12/2003 |
| JP | 6-327770 A | 11/1994 | | WO | WO 2004/007554 A1 | 1/2004 |
| JP | 7-222799 A | 8/1995 | | WO | WO 2004/011065 A1 | 2/2004 |
| JP | 8-502180 T | 3/1996 | | WO | WO 2004/030732 A2 | 4/2004 |
| JP | 8-504354 T | 5/1996 | | WO | WO 2004/035117 A2 | 4/2004 |
| JP | 9-225029 A | 9/1997 | | WO | WO 2004/047890 A1 | 6/2004 |
| JP | 10-504474 T | 5/1998 | | WO | WO 2004/047891 A1 | 6/2004 |
| JP | 10-507935 | 8/1998 | | WO | WO 2004/047892 A | 6/2004 |
| JP | 11-503637 T | 3/1999 | | WO | WO 2004/054645 A3 | 7/2004 |
| JP | 11-504536 T | 4/1999 | | WO | WO 2004/087242 A1 | 10/2004 |
| JP | 11-164887 T | 6/1999 | | WO | WO 2004/108194 A1 | 12/2004 |
| JP | 11-512332 T | 10/1999 | | WO | WO 2005/009515 A1 | 2/2005 |
| JP | 2000-510021 T | 8/2000 | | WO | WO 2005/023341 A1 | 3/2005 |
| JP | 2002-500933 T | 1/2002 | | WO | WO 2005/025636 A2 | 3/2005 |
| JP | 2002-095749 A | 4/2002 | | WO | WO 2005/030301 A1 | 4/2005 |
| JP | 2002-513547 T | 5/2002 | | WO | WO 2005/035028 A1 | 4/2005 |
| JP | 2002-526175 A | 8/2002 | | WO | WO 2005/044345 A | 5/2005 |
| JP | 2002-528182 T | 9/2002 | | WO | WO 2005/044347 A1 | 5/2005 |
| JP | 2002-532161 T | 10/2002 | | WO | WO 2005/058396 A1 | 6/2005 |
| JP | 2003-511105 T | 3/2003 | | WO | WO 2005/070481 A | 8/2005 |
| JP | 2003-532500 T | 11/2003 | | WO | WO 2005/082438 A1 | 9/2005 |
| JP | 2003-533288 A | 11/2003 | | WO | WO 2005/097238 A3 | 10/2005 |
| JP | 2004-533282 T | 11/2004 | | WO | WO 2005/115507 A1 | 12/2005 |
| JP | 2004-33737 A | 8/2005 | | WO | WO 2005/115508 A1 | 12/2005 |
| NZ | 573171 A | 11/2010 | | WO | WO 2005/115509 A1 | 12/2005 |
| NZ | 573350 A | 12/2010 | | WO | WO 2005/115510 A1 | 12/2005 |
| WO | WO 88/10129 A1 | 12/1988 | | WO | WO 2005/115512 A1 | 12/2005 |
| WO | WO 98/10129 A1 | 12/1988 | | WO | WO 2005/115513 A1 | 12/2005 |
| WO | WO 92/19296 A | 11/1992 | | WO | WO 2005/115514 A1 | 12/2005 |
| WO | WO 93/02186 A1 | 2/1993 | | WO | WO 2005/120607 A2 | 12/2005 |
| WO | WO 93/21986 A2 | 11/1993 | | WO | WO 2006/044236 A2 | 4/2006 |
| WO | WO 93/23098 A1 | 11/1993 | | WO | WO 2006/050304 A1 | 5/2006 |

| | | |
|---|---|---|
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/122193 A1 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 88/08725 | 11/2008 |

OTHER PUBLICATIONS

International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.

European Search Report dated Feb. 1, 2006; Application No. 05255298.1.
Great Britain Search Report dated Sep. 22, 2006; Application No. GB0610860.9.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11170040.

* cited by examiner

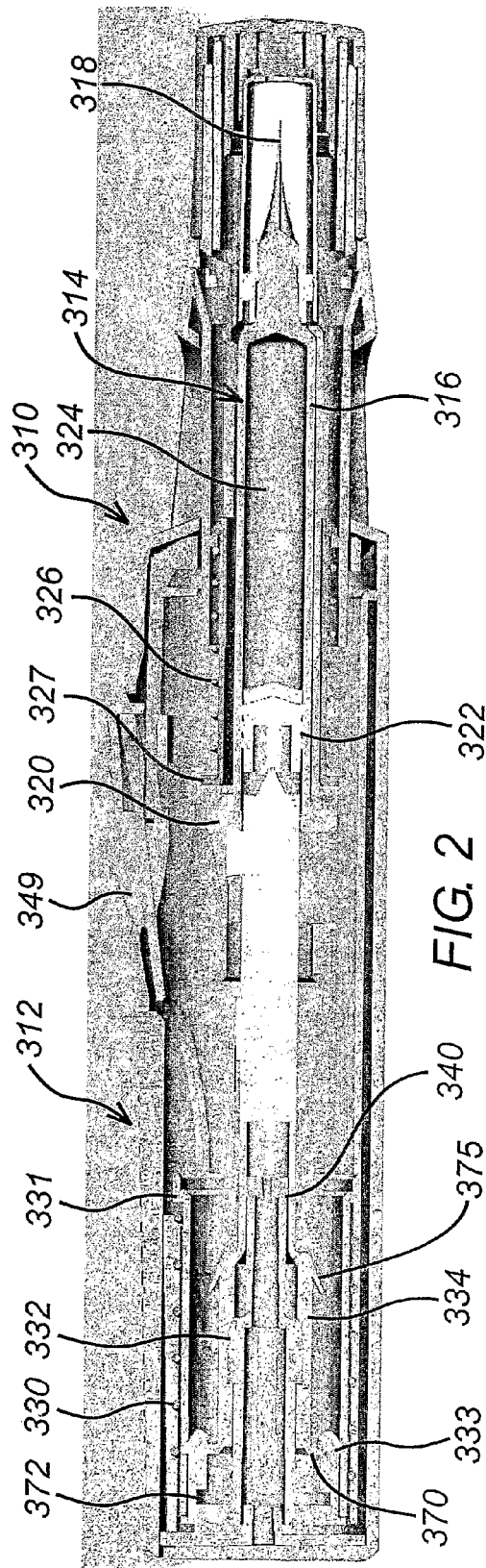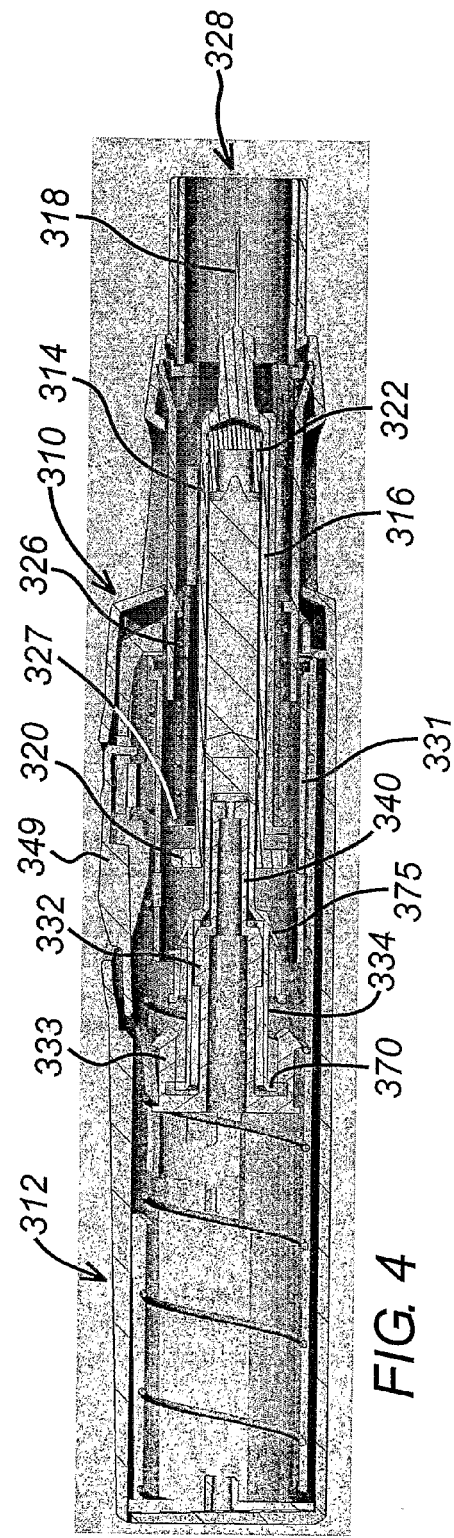

INJECTION DEVICE

The present application claims the benefit and priority to and is a U.S. National Phase of PCT International Application Number PCT/GB2005/002137, filed on May 27, 2005, which claims priority to United Kingdom Application No. 0412061.4, filed May 28, 2004, both of which are expressly incorporated by reference in their entirety.

BACKGROUND TECHNOLOGY

The present invention relates to an injection device of the type that receives a syringe, extends it, discharges its contents and then retracts it automatically. Devices of this general description are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

In devices of this nature, it is desirable for the return spring to be sufficiently strong that it can retract the syringe quickly. However, it is then possible for the syringe to be retracted so forcefully that it escapes from those elements of the device that are supposed to hold it during the extension and retraction phases. The syringe may then be free to move around within the body of the device. This gives rise to a number of undesirable effect. Firstly, the syringe will rattle around in the body of the device, giving an impression of poor quality. Secondly, shaking the device, which may be encouraged in those patients of a certain disposition by the rattling noise made by the syringe, might break the syringe, allowing broken glass to escape. Moreover, if the device has a viewing window, through which the discharged syringe may be inspected, the syringe will no longer be correctly positioned relative to it.

SUMMARY OF THE INVENTION

It is an objective of the present invention to provide an improved injection device that does not suffer from these shortcomings.

Accordingly, the present invention provides an injection device comprising:
 a housing adapted to receive a syringe having a discharge nozzle and including means for biasing the syringe from an extended position in which the discharge nozzle of the syringe extends from the housing to a retracted position in which the discharge nozzle is contained within the housing;
 an actuator;
 a drive acted upon by the actuator and in turn acting on the syringe to advance it from its retracted position to its extended position and discharge its contents through the discharge nozzle;
 a release mechanism, activated when the drive has been advanced to a nominal release position, to release the syringe from the action of the actuator, whereupon the biasing means restores the syringe to its retracted position; and
 a locking mechanism that confines the returned syringe in its retracted position.

By confining the syringe in its retracted position, rather than permitting it to break free, the present invention overcomes the disadvantages discussed above. Preferably, the locking mechanism is activated when the drive has been advanced to a locking position that is no more advanced than the said nominal release position.

In a preferred implementation of the present invention, the housing includes a syringe carrier adapted to receive the syringe and the biasing means is adapted to bias the syringe carrier from an extended position to a retracted position. In that case, the locking mechanism can prevent the drive from retracting relative to the syringe carrier, thus confining the syringe between the drive and the syringe carrier in preparation for the activation of the release mechanism.

Con convenience of manufacture and simplicity of operation, the drive may include a flexible latch that rides over a detent as the drive is advanced and thereafter engages beyond it. For example, the syringe carrier may include a detent and the flexible latch may ride over the detent as the drive is advanced and thereafter engage beyond it. The flexible latch may comprises a flexible barb, for increased security of latching.

A plurality of such flexible latches may be present, and they can be substantially equidistantly spaced around the circumference of the drive.

BRIEF DESCRIPTION OF THE DRAWINGS

The invention will now be described by way of example with reference to the accompanying drawings, in which:
FIGS. 2-4 show an embodiment of the present invention.

DETAILED DESCRIPTION

Figure 1:
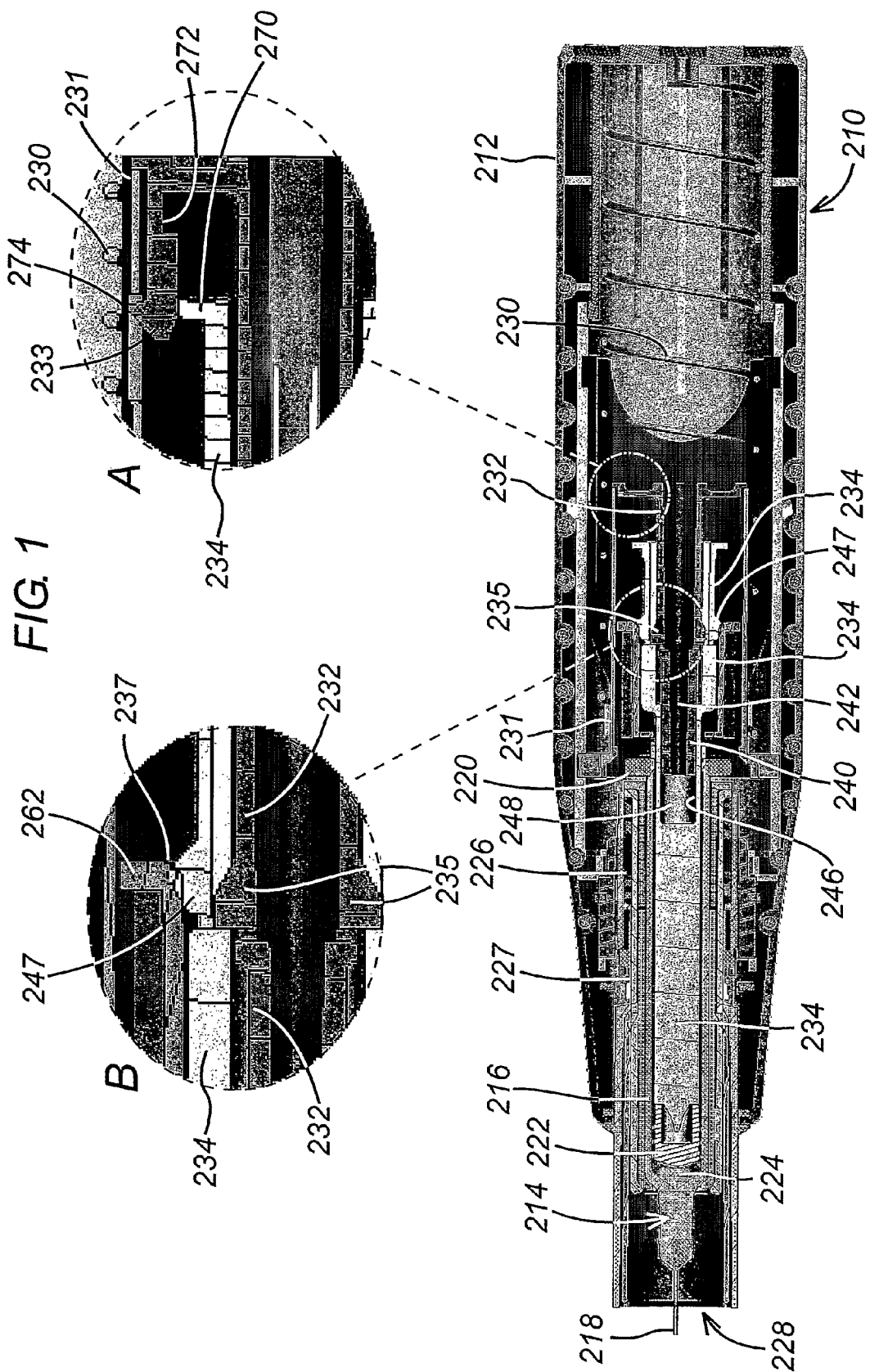
FIG. 1 is an illustration of a comparative injection device as discussed above.

FIG. 1 shows an injection device 210 in which a housing 212 contains a hypodermic syringe 214. The syringe 214 is again of conventional type, including a syringe body 216 terminating at one end in a hypodermic needle 218 and at the other in a flange 220, and a rubber bung 222 that constraints a drug 224 to be administered within the syringe body 216. The conventional plunger that would normally be connected to the bung 222 and used to discharge the contents of the syringe 214 manually, has been removed and replaced with a multi-component drive element as will be described below. Whilst the syringe illustrated is again of hypodermic type, this need not necessarily be so. As illustrated, the housing includes a return spring 226 that biases the syringe 214 from an extended position in which the needle 218 extends from aperture 228 in the housing 212, to a retracted position in which the hypodermic needle 218 is contained within the housing 212. The return spring 226 acts on the syringe 214 via a sleeve 227.

At the other end of the housing is a compression drive spring 230. Drive from the drive spring 230 this transmitted via the multi-component drive to the syringe 214 to advance it from its retracted position to its extended position and discharge its contents through the needle 218. The drive accomplishes this task by acting directly on the drug 224 and the syringe 214. Hydrostatic forces acting through the drug 224 and, to a lesser extent, static friction between the bung 222 and the syringe body 216 initially ensures that they advance together, until the return spring 226 bottoms out or the syringe body 216 meets some other obstruction that retards its motion.

The multi component drive between the drive spring 230 and the syringe 214 again consists of three principal components. The drive sleeve 231 takes drive from the drive spring 230 and transmits it to flexible latch arms 233 on a first drive element 232. These elements are shown in detail "A". The first drive element 232 in turn transmits drive via flexible latch arms 235 to a second drive element 234. These elements are shown in detail "B". As before, the first drive element 232 includes a hollow stem 240, the inner cavity of which forms a collection chamber 242. The second drive element 234 includes a blind for 246 that is open at one end to receive the stem 240 and closed at the other. As can be seen, the bore 246 and the stem 240 define a fluid reservoir 248, within which a damping fluid is contained.

A trigger (not shown) is provided at the middle of the housing 212 and, one operated, serves to decouple the drive sleeve 231 from the housing 212 allowing it to move relative to the housing 212 under the influence of the drive spring 230. The operation of the device is then as follows.

Initially, the drive spring 230 moves the drive sleeve 231, the drive sleeve 231 moves the first drive element 232 and the first drive element 232 moves the second drive element 234, in each case by acting through the flexible matching arms 233, 235. The second drive element 234 moves and, by virtue of static friction and hydrostatic forces acting through the drug 224 to be administered, moves the syringe body 216 against the action of the return spring 226. The return spring 226 compresses and the hypodermic needle 218 emerges from the exit aperture 228 of the housing 212. This continues until the return spring 226 bottoms out or the syringe body 216 meets some other obstruction that retards its motion. Because the static friction between the bung 222 and the syringe body 216 and the hydrostatic forces acting through the drug 224 to be administered are not sufficient to resist the full drive force developed by the drive spring 230, at this point the second drive element 234 begins to move within the syringe body 216 and the drug 224 begins to be discharged. Dynamic friction between the bung 222 and the syringe body 216 and hydrostatic forces acting through the drug 224 to be administered are, however, sufficient to retain the return spring 226 in its compressed state, so the hypodermic needle 218 remains extended.

Before the second drive element 234 reaches the end of its travel within the syringe body 216, so before the contents of the syringe have fully discharged, the flexible latch arms 235 linking the first and second drive elements 232, 234 reach a constriction 237. The constriction 237 is formed by a component 262 that is initially free to move relative to all other components, but that is constrained between the syringe flange 220 and additional flexible arms 247 on the second drive element 234. These additional flexible arms 247 overlie the flexible arms 235 on the first drive element 232, by means of which drive is transmitted to the second drive element 234. FIG. 1 illustrates the injection device 210 at the position where the additional flexible arms 247 are just making contact with the constriction 237 in the component 262.

The constriction 237 moves the additional flexible arms 247 inwards, aided by the bevelled surfaces on both, and the additional flexible arms 247 in turn move the flexible arms 235, by means of which drive is transmitted from the first drive element 232 to the second drive element 234, inwards from the position shown to a position at which they no longer couple the first and second drive elements together. Once this happens, the first drive element 232 acts no longer on the second drive element 234, allowing the first drive element 232 to move relative to the second drive element 234.

Because the damping fluid is contained within a reservoir 248 defined between the end of the first drive element 232 and the blind bore 246 in the second drive element 234, the volume of the reservoir 248 will tend to decrease as the first drive element 232 moves relative to the second drive element 234 when the former is acted upon by the drive spring 230. As the reservoir 248 collapses, damping fluid is forced into the collection chamber 242. Thus, once the flexible latch arms 235 have been released, the force exerted by the drive spring 230 does work on the damping fluid, causing it to flow into the collection chamber 242, and also acts hydrostatically through the fluid and through friction between the first and second drive elements 232, 234, thence via the second drive element 234. Losses associated with the flow of the damping fluid do not attenuate the force acting on the body of the syringe to a great extent. Thus, the return spring 226 remains compressed and the hypodermic needle remains extended.

After a time, the second drive element 234 completes its travel within the syringe body 216 and can go no further. At this point, the contents of the syringe 214 are completely discharged and the force exerted by the drive spring 230 acts to retain the second drive element 234 in its terminal position and to continue to cause the damping fluid to flow into the collection chamber 242, allowing the first drive element 232 to continue its movement.

A flange 270 on the rear of the second drive element 234 normally retains the flexible arms 233 in engagement with the drive sleeve 231. However, before the reservoir 248 of fluid is exhausted, the flexible latch arms 233 linking the drive sleeve 231 with the first drive element 232 move sufficiently far forward relative to the second drive element 234 that the flange 270 is brought to register with a rebate 272 in the flexible arms 233, whereupon it ceases to be effective in retaining the flexible arms 233 in engagement with the drive sleeve 231. Now, the drive sleeve 231 moves the flexible latch arms 233 inwards from the position shown to a position at which they no longer couple the drive sleeve 231 to the first drive element 232, aided by the bevelled latching surfaces 274 on the flexible arms 233. Once this happens, the drive sleeve 231 acts no longer on the first drive element 232, allowing them to move relative to each other. At this point, of course, the syringe 214 is released, because the forces developed by the drive spring 230 are no longer being transmitted to the syringe 214, and the only force acting on the syringe will be the return force from the return spring 226. Thus, the syringe 214 now returns to its retracted position and the injection cycle is complete.

However, in this example, it may be possible for the syringe to return beyond its retracted position, or in other words to come free of the syringe carrier and then rattle around within the body of the injection device. Although there is of course no possibility of the syringe falling out of the injection device altogether, the various undesirable consequences that have already been discussed may follow.

Figure 3:
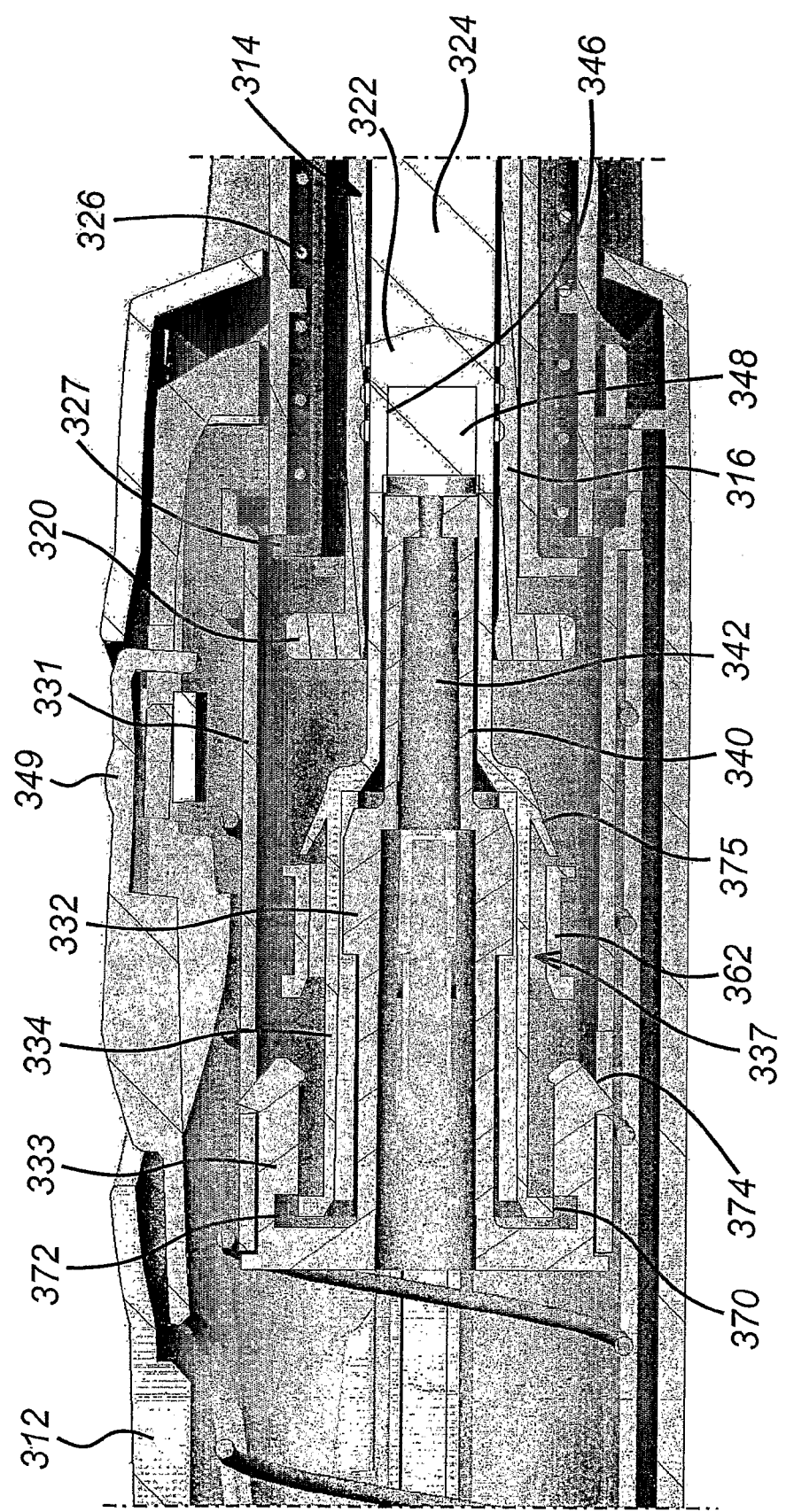

FIGS. 2-4 show an injection device 310 in which this problem is neatly overcome. Again, a housing 312 contains a hypodermic syringe 314. The syringe 314 is again of conventional type, including a syringe body 316 terminating at one end in a hypodermic needle 318 and at the other in a flange 320, and a rubber bung 322 that constraints a drug 324 to be administered within the syringe body 316. Whilst the syringe illustrated is again of hypodermic type, this need not necessarily be so. As illustrated, the housing includes a return spring 326 that biases the syringe 314 from an extended position in which the needle 318 extends from an aperture 328 in the housing 312, to a retracted position in which the hypodermic needle 318 is contained within the housing 312. The return spring 326 acts on the syringe 314 via a sleeve 327. The extended position of the syringe 314 is shown in FIG. 3; and the retracted position, after the injection cycle is complete is shown in FIG. 4.

At the other end of the housing is a compression drive spring 330. Drive from the drive spring 330 this transmitted via the multi-component drive to the syringe 314 to advance it from its retracted position to its extended position and discharge its contents through the needle 318. The drive accomplishes this task by acting directly on the drug 324 and the syringe 314. Hydrostatic forces acting through the drug and, to a lesser extent, static friction between the bung 322 and the syringe body 316 initially ensures that they advance together, until the return spring 326 bottoms out or the syringe body 316 meets some other obstruction that retards its motion.

The multi component drive between the drive spring 330 and the syringe 314 again consists of three principal components. The drive sleeve 331 takes drive from the drive spring 330 and transmits it to flexible latch arms 333 on a first drive element 332. The first drive element 332 in turn transmits drive via flexible latch arms (not shown) to a second drive element 334. As before, the first drive element 332 includes a hollow stem 340, the inner cavity of which forms a collection chamber 342. The second drive element 334 includes a blind bore 346 that is open at one end to receive the stem 340 and closed at the other. As can be seen, the bore 346 and the stem 340 define a fluid reservoir 348, within which a damping fluid is contained.

A trigger 349 is provided in the housing 312. The trigger 349, one operated, serves to decouple the drive sleeve 331 from the housing 312 allowing it to move relative to the housing 312 under the influence of the drive spring 330. The operation of the device is then as follows.

Initially, the drive spring 330 moves the drive sleeve 331, the drive sleeve 331 moves the first drive element 332 and the first drive element 332 moves the second drive element 334, in each case by acting through the flexible matching arms (not shown). The second drive element 334 moves and, by virtue of static friction and hydrostatic forces acting through the drug 324 to be administered, moves the syringe body 316 and hence the sleeve 327 against the action of the return spring 326. The return spring 326 compresses and the hypodermic needle 318 emerges from the exit aperture 328 of the housing 312. This continues until the return spring 326 bottoms out or the sleeve 327 meets some other obstruction that retards its motion. Because the static friction between the bung 322 and the syringe body 316 and the hydrostatic forces acting through the drug 324 to be administered are not sufficient to resist the full drive force developed by the drive spring 330, at this point the second drive element 334 begins to move within the syringe body 316 and the drug 324 begins to be discharged. Dynamic friction between the bung 322 and the syringe body 316 and hydrostatic forces acting through the drug 324 to be administered are, however, sufficient to retain the return spring 326 in its compressed state, so the hypodermic needle 318 remains extended.

Before the second drive element 334 reaches the end of its travel within the syringe body 316, so before the contents of the syringe have fully discharged, the flexible latch arms (not shown) linking the first and second drive elements 332, 334 reach a constriction 337. The constriction 337 is formed by a component 362 that is formed integrally with the syringe carrier. As before, additional flexible arms (not shown) on the second drive element 334 overlie the flexible arms (not shown) on the first drive element 332, by means of which drive is transmitted to the second drive element 334.

In the same way as for FIG. 1, the constriction 337 causes the first and second drive elements 332, 334 to disengage. In addition, the constriction 337 serves a second purpose. To this end, the second drive element 334 is provided with a pair of oblique flexible barbs 375. In their rest position, the barbs extend from the second drive element 334 to a diameter that is larger than the inner diameter of the constriction 337. As the second drive element advances, oblique flexible barbs 375 are pressed down against the second drive element 334, and pass thought the constriction 337. Once they have passed through it, they spring back to their rest position. Because, in that position, they extend from the second drive element 334 to a diameter that is larger than the inner diameter of the constriction 337, any attempt to move the second drive element 334 backwards through the constriction 337 will result in the flexible barbs 375 being splayed outwards, preventing the backward motion. Thus, the flexible barbs 375 and the constriction 337 together form a non-return mechanism.

Because the damping fluid is contained within a reservoir 348 defined between the end of the first drive element 332 and the blind bore 346 in the second drive element 334, the volume of the reservoir 348 will tend to decrease as the first drive element 332 moves relative to the second drive element 334 when the former is acted upon by the drive spring 330. As the reservoir 348 collapses, damping fluid is forced into the collection chamber 342. Thus, once the flexible latch arms (not shown) have been released, of the force exerted by the drive spring 330 does work on the damping fluid, causing it to flow into the collection chamber 342, and also acts hydrostatically through the fluid and through friction between the first and second drive elements 332, 334, thence via the second drive element 334. Losses associated with the flow of the damping fluid do not attenuate the force acting on the body of the syringe to a great extent. Thus, the return spring 326 remains compressed and the hypodermic needle remains extended.

After a time, the second drive element 334 completes its travel within the syringe body 316 and can go no further. At this point, the contents of the syringe 314 are completely discharged and the force exerted by the drive spring 330 acts to retain the second drive element 334 in its terminal position and to continue to cause the damping fluid to flow into the collection chamber 342, allowing the first drive element 332 to continue its movement.

A flange 370 on the rear of the second drive element 334 normally retains the flexible arms 333 in engagement with the drive sleeve 331. However, before the reservoir 348 of fluid is exhausted, the flexible latch arms 333 linking the drive sleeve 331 with the first drive element 332 move sufficiently far forward relative to the second drive element 334 that the flange 370 is brought to register with a rebate 372 in the flexible arms 333, whereupon it ceases to be effective in retaining the flexible arms 333 in engagement with the drive sleeve 331. Now, the drive sleeve 331 moves the flexible latch arms 333 inwards from the position shown to a position at which they no longer couple the drive sleeve 331 to the first drive element 332, aided by the bevelled latching surfaces 374 on the flexible arms 333. Once this happens, the drive sleeve 331 acts no longer on the first drive element 332, allowing them to move relative to each other. At this point, of course, the syringe 314 is released, because the forces developed by the drive spring 330 are no longer being transmitted to the syringe 314, and the only force acting on the syringe will be the return force from the return spring 326. Thus, the syringe 314 now returns to its retracted position and the injection cycle is complete.

The non-return mechanism formed by the barbs 375 and the constriction 337 at all times constrains the syringe between the drive and the syringe carrier, thus preventing it from coming loose within the body of the injection device.

The invention claimed is:
1. An injection device comprising:
a housing adapted to receive a syringe having an elongate syringe body terminating at a distal end in a discharge nozzle and at a proximal end in a flange, and having a bung that constrains a drug to be administered within the elongate syringe body distal of the bung, the elongate syringe body, discharge nozzle, flange and bung being coaxially aligned along a longitudinal axis, the housing including means for biasing the syringe from an extended position in which the discharge nozzle of the syringe extends from the housing to a retracted position in which the discharge nozzle is contained within the housing;

a drive spring;

a drive acted upon by the drive spring and in turn acting on the syringe to advance it from its retracted position to its extended position and discharge its contents through the discharge nozzle;

a release mechanism, activated when the drive has been advanced to a nominal release position, to release the syringe from the action of the drive spring, whereupon the biasing means restores the syringe to its retracted position; and a locking mechanism that confines the returned syringe in its retracted position wherein:

the housing includes a syringe carrier adapted to receive the syringe;

the biasing means is adapted to bias the syringe carrier from an extended position to a retracted position; and the locking mechanism prevents the drive from retracting relative to the syringe carrier, thus confining the syringe between the drive and the syringe carrier.

2. An injection device according to claim 1 in which the locking mechanism is activated when the drive has been advanced to a locking position that is no more advanced than the said nominal release position.

3. An injection device according to claim 2, in which the drive includes a flexible latch that rides over a detent as the drive is advanced and thereafter engages beyond it.

4. An injection device according to claim 1, in which:
the syringe carrier includes a detent; and
the drive includes a flexible latch that rides over the detent as the drive is advanced and thereafter engages beyond it.

5. An injection device according to claim 3 in which the flexible latch comprises a flexible barb.

6. An injection device according to claim 3 including a plurality of such flexible latches.

7. An injection device according to claim 6 in which the flexible latches are substantially equidistantly spaced around the circumference of the drive.

8. An injection device according to claim 1 in which the drive includes first and second drive elements, of which the first is acted upon by the actuator and in turn acts upon the second, and the second acts upon the syringe or the syringe carrier to advance it from its retracted position to its extended position and discharge its contents through the discharge nozzle, the first drive element being capable of movement relative to the second when the first is acted upon by the drive spring and the second is restrained by the syringe or the syringe carrier.

9. An injection device according to claim 8, further comprising a coupling that prevents the first drive element from moving relative to the second until they have been advanced to a nominal decoupling position that is less advanced than the said nominal release position.

10. An injection device according to claim 9 in which the coupling comprises a decoupling mechanism, activated when the drive elements have been advanced to the said nominal decoupling position and adapted to decouple the first drive element from the second, thus allowing the first drive element to move relative to the second.

* * * * *